(12) United States Patent
Glick et al.

(10) Patent No.: US 6,780,871 B2
(45) Date of Patent: Aug. 24, 2004

(54) METHODS AND COMPOSITIONS FOR TREATING ADDICTION DISORDERS

(75) Inventors: Stanley D. Glick, Delmar, NY (US); Isabelle M. Maisonneuve, Delmar, NY (US)

(73) Assignee: Albany Medical College, Albany, NY (US)

(*) Notice: Subject to any disclaimer, the term of this patent is extended or adjusted under 35 U.S.C. 154(b) by 0 days.

(21) Appl. No.: 10/051,770

(22) Filed: Jan. 18, 2002

(65) Prior Publication Data

US 2002/0103109 A1 Aug. 1, 2002

Related U.S. Application Data

(60) Provisional application No. 60/264,742, filed on Jan. 29, 2001.

(51) Int. Cl.[7] .......................... A61K 31/44; A61K 9/70; A61K 31/55; A61K 31/542
(52) U.S. Cl. .................. 514/282; 514/343; 514/214.03; 514/226.2
(58) Field of Search ................................ 514/343, 282, 514/214.03, 226.2

(56) References Cited

U.S. PATENT DOCUMENTS

| | | | |
|---|---|---|---|
| 5,654,281 A | 8/1997 | Mayer et al. | |
| 5,863,927 A | 1/1999 | Smith et al. | |
| 5,965,567 A | 10/1999 | Archer et al. | |
| 6,211,360 B1 | 4/2001 | Glick et al. | |

FOREIGN PATENT DOCUMENTS

WO    WO 99/17803    4/1999

OTHER PUBLICATIONS

Murray et al., "Interaction of Dextrorotary Opioids with Phencyclidine Recognition Sites in Rat Brain Membranes," *Life Sci.*, 34:1899–1911 (1984).

Nishikawa et al., "Evidence for, and Nature of, the Tonic Inhibitory Influence of Habenulointerpeduncular Pathways upon Cerebral Dopaminergic Transmission in the Rat," *Brain Res.*, 373:324–336 (1986).

(List continued on next page.)

*Primary Examiner*—Marianne C. Seidel
*Assistant Examiner*—Brian-Yong S. Kwon
(74) *Attorney, Agent, or Firm*—Rogalskyj & Weyand, LLP

(57) ABSTRACT

A method for treating an addiction disorder (such as an addiction to or dependency on stimulants, nicotine, morphine, heroin, other opiates, amphetamines, cocaine, and/or alcohol) in a patient is disclosed. The method includes administering to the patient a first $\alpha_3\beta_4$ nicotinic receptor antagonist and administering to the patient a second $\alpha_3\beta_4$ nicotinic receptor antagonist. The second $\alpha_3\beta_4$ nicotinic receptor antagonist is different than the first $\alpha_3\beta_4$ nicotinic receptor antagonist, and the first $\alpha_3\beta_4$ nicotinic receptor antagonist and the second $\alpha_3\beta_4$ nicotinic receptor antagonist are administered simultaneously or non-simultaneously. Compositions which include a first $\alpha_3\beta_4$ nicotinic receptor antagonist and a second $\alpha_3\beta_4$ nicotinic receptor antagonist are also described. Examples of suitable $\alpha_3\beta_4$ nicotinic receptor antagonists for use in the present invention's methods and compositions include mecamylamine, 18-methoxycoronaridine, bupropion, dextromethorphan, dextrorphan, and phamaceutically acceptable salts and solvates thereof. A method of evaluating a compound for its effectiveness in treating addiction disorders is also described.

56 Claims, 7 Drawing Sheets

OTHER PUBLICATIONS

Koyuncuoglu et al., "The Treatment of Heroin Addicts with Dextromethorphan: A Double–blind Comparison of Dextromethrophan with Chlorpromazine," *Int. J. Clin. Pharmacol. Ther.*, 28:147–152 (1990).

Glick et al., "Effects and Aftereffects of Ibogaine on Morphine Self–administration in Rats," *Europ. J. Pharmacol.*, 195:341–345 (1991).

Flores et al., "A Subtype of Nicotinic Cholinergic Receptor in Rat Brain Is Comprised of 4 and 2 Subunits and Is Up–regulated by Chronic Nicotine Treatment," *Mol. Pharmacol.*, 41:31–37 (1992).

Koyuncuoglu, "The Combination of Tizanidine Markedly Improves the Treatment with Dextromethorphan of Heroin Addicted Outpatients," *Int. J. Clin. Pharmacol. Ther.*, 33:13–19 (1995).

Popik et al., "NMDA Antagonist Properties of the Putative Antiaddictive Drug, Ibogaine," *J. Pharmacol. Exp. Ther.*, 275–753–760 (1995).

Sweetnam et al., "Receptor Binding Profile Siggest Multiple Mechanisms of Action Are Responsible for Ibogaine's Putative Anti–addictive Activity," *Psychopharmacology*, 118:369–376 (1995).

Chen et al., "Ibogaine Block of the Nmda Receptor: in Vitro and in Vivo Studies," *Neuropharmacology*, 35:423–431 (1996).

Glick et al., "18–Methoxycoronaridine, a Non–toxic Iboga Alkaloid Congener: Effects of Morphine and Cocaine Self–administration and on Mesolimbic Dopamine Release in Rats," *Brain Res.*, 719:29–35 (1996).

Badio et al., "Ibagaine: A Potent Noncompetitive Blocker of Ganglionic/Neuronal Nicotinic Receptors," *Molec. Pharmacol.*, 51:1–5 (1997).

Pulvirenti et al., "Dextromethorphan Reduces Intravenous Cocaine Self–administration in the Rat," *Eur. J. Pharmacol.*, 321:279–283 (1997).

Rezvani et al., "Attenuation of Alcohol Consumption by a Novel Non–toxic Ibogaine Analog (18–Methoxycoronaridine) in Alcohol Preferring Rats," *Pharmacol. Biochem. Behav.*, 58:615–619 (1997).

Ebert et al., "Opioid Analgesics as Noncompetitive N–methyl–d–aspartate (NMDA) Antagonists," *Biochem. Pharmacol.*, 56:533–559 (1998).

Glick et al., "Mechanisms of Anti–addictive Actions of Ibogaine," *Ann. N.Y. Acad. Sci.*, 844, 214–226 (1998).

Mah et al., "Ibogaine Acts at the Nicotinic Acetylcholine Receptor to Inhibit Catecholamine Release," *Brain Res.*, 797:173–180 (1998).

Fryer et al., "Noncompetitive Functional Inhibition at Diverse , Human Nicotinic Acetylcholine Receptor Subtypes by Bupropion, Phencyclidine, and Ibogaine," *J. Pharmacol. Exp. Ther.*, 288:88–92 (1999).

Lukas et al., "International Union of Pharmacology, XX, Current Status of the Nomenclature for Nicotinic Acetylcholine Receptors and Their Subunits," *Pharmacol. Rev.*, 51:397–401 (1999).

Maisonneuve et al., "Attenuation of the Reinforcing Efficacy of Morphine by 18–Methoxycoronaridine," *Euro. J. Pharmacol.*, 383:15–21 (1999).

Quick et al., "3 4 Subunit–containing Nicotinic Receptors Dominate Function in Rat Medial Habenula Neurons," *Neuropharmacology*, 38:769–783 (1999).

Reid et al., "A Nicotinic Antagonist, Mecamylamine, Reduces Cue–induced Craving in Cocaine–dependent Subjects," *Neuropsychopharmacology*, 20:297–307 (1999).

Glick et al., "18–MC Reduces Methamphetamine and Nicotine Self–Administration in Rats," *NeuroReport*, 11:2013–2015 (2000).

Glick et al., "18–Methoxycoronaridine (18–MC) and Ibogaine: Comparison of Anti–addictive Efficacy, Toxicity and Mechanisms of Action," *Ann. N.Y. Acad. Sci.*, 914:369–387 (2000).

Glick et al., "Development of Novel Medication for Drug Addicition: The Legacy of an African Shrub," *Ann. N.Y. Acad. Sci.* , 909:88–103 (2000).

Hernandez et al., "Dextromethorphan and its Metabolite Dextrorphan Block 3 4 Neuronal Nicotinic Receptors," *J. Pharmacol. Exp. Ther.*, 293:962–967 (2000).

Jun et al., "Dextromethorphan Alters Methamphetamine Self–Administration in the Rat," *Pharmacol. Biochem. Behav.*, 67:405–409 (2000).

Levin et al., "Mecamylamine Preferentially Inhibits Cocaine Versus Food Self–administration in Rats," *Soc. Neurosci. Abstr.*, 26:1821 (2000).

Glick et al., "Comparative Effects of Dextromethorphan and Dextrorphan on Morphine, Methamphetamine, and Nicotine Self–administration in Rats," *Europ. J. Pharmacol.*, 422:87–90 (2001).

Klink et al., "Molecular and Physiological Diversity of Nicotinic Acetylcholine Receptors in the Midbrain Dopaminergic Nuclei, " *J. Neurosci.*, 21:1452–1463 (2001).

Papke et al., "Analysis of Mecamylamine Steroisomers on Human Nicotinic Receptor Subtypes," *J. Pharmacol. Exp. Ther.*, 297:646–656 (2001).

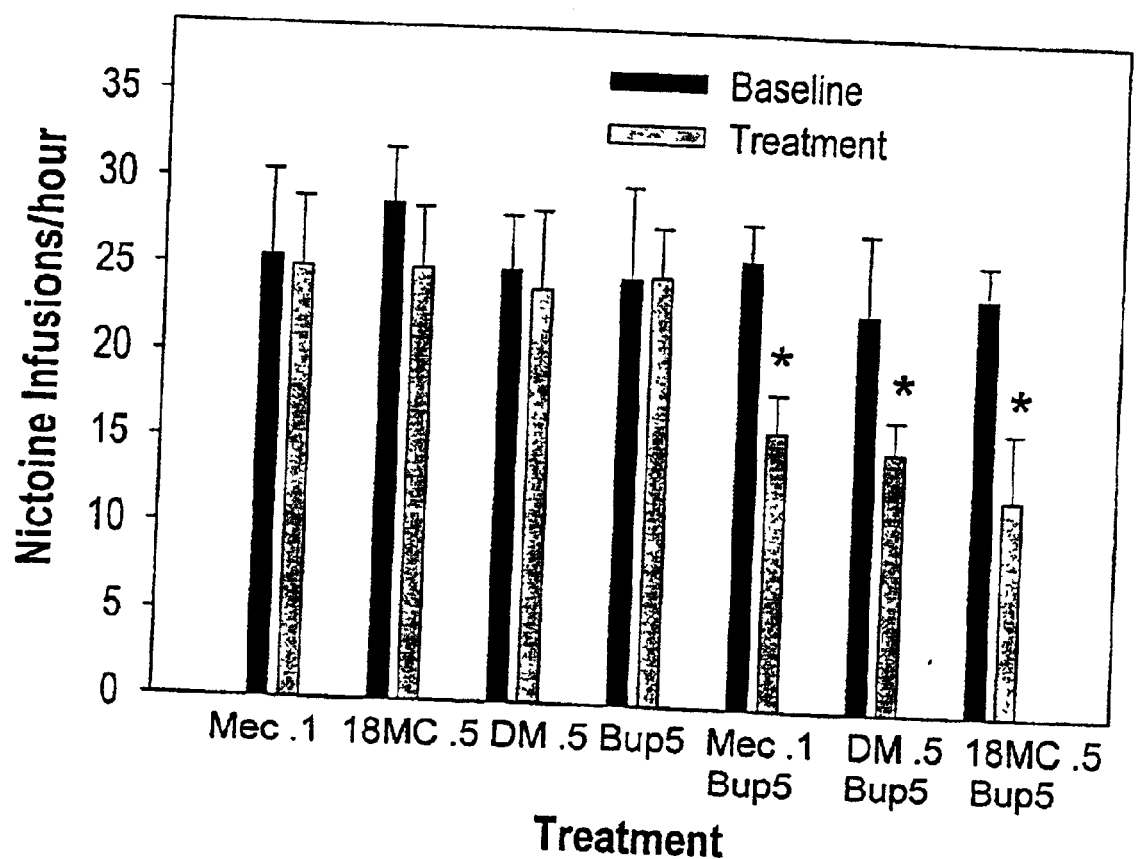

US 6,780,871 B2

METHODS AND COMPOSITIONS FOR TREATING ADDICTION DISORDERS

The present invention claims the benefit of U.S. Provisional Patent Application Serial No. 60/264,742, filed Jan. 29, 2001, which is hereby incorporated by reference.

The present invention was made with the support of the National Institute on Drug Abuse Grant No. DA 03817. The Federal Government may have certain rights in this invention.

FIELD OF THE INVENTION

The present application relates, generally, to methods of treating addiction disorders using $\alpha_3\beta_4$ nicotinic receptor antagonists and to compositions useful in such treatments.

BACKGROUND OF THE INVENTION

Drug and alcohol addiction and/or abuse and/or dependency (collectively referred to herein as "addiction disorders") is extremely common. Individuals suffering from such addictions are generally subject to significant symptoms of withdrawal upon attempting to cease use of the addictive substance (whether alcohol or drugs such as cocaine, heroine, nicotine, painkillers, etc.). A number of medical therapies have been tried with differing levels of success. Unfortunately, to date, none of these methods of treatment have been very successful. For this and other reasons, a need exists for improved methods for treating addictive disorders.

SUMMARY OF THE INVENTION

The present invention relates to a method for treating an addiction disorder in a patient. The method includes administering to the patient a first $\alpha_3\beta_4$ nicotinic receptor antagonist and administering to the patient a second $\alpha_3\beta_4$ nicotinic receptor antagonist. The second $\alpha_3\beta_4$ nicotinic receptor antagonist is different than the first $\alpha_3\beta_4$ nicotinic receptor antagonist, and the first $\alpha_3\beta_4$ nicotinic receptor antagonist and the second $\alpha_3\beta_4$ nicotinic receptor antagonist are administered simultaneously or non-simultaneously.

The present invention also relates to a composition which includes a first $\alpha_3\beta_4$ nicotinic receptor antagonist and a second $\alpha_3\beta_4$ nicotinic receptor antagonist. In this composition, the second $\alpha_3\beta_4$ nicotinic receptor antagonist is different than the first $\alpha_3\beta_4$ nicotinic receptor antagonist.

The present invention also relates to a composition which includes a first compound selected from the group consisting of mecamylamine, 18-methoxycoronaridine, bupropion, dextromethorphan, dextrorphan, and phamaceutically acceptable salts and solvates thereof; and a second $\alpha_3\beta_4$ compound selected from the group consisting of mecamylamine, 18-methoxycoronaridine, bupropion, dextromethorphan, dextrorphan, and phamaceutically acceptable salts and solvates thereof. In this composition, the second compound is different than the first compound.

The present invention also relates to a method of evaluating a compound for its effectiveness in treating addiction disorders by assessing the compound's ability to bind to $\alpha_3\beta_4$ nicotinic receptors.

The present invention also relates to a method for treating an addiction disorder in a patient. The method includes administering to the patient an $\alpha_3\beta_4$ nicotinic receptor antagonist under conditions effective to treat the patient's addiction disorder.

BRIEF DESCRIPTION OF THE DRAWINGS

FIG. 12 is a bar graph showing the effects of various drugs and drug combinations on nicotine self-administration.

DETAILED DESCRIPTION OF THE INVENTION

Figure 1A:
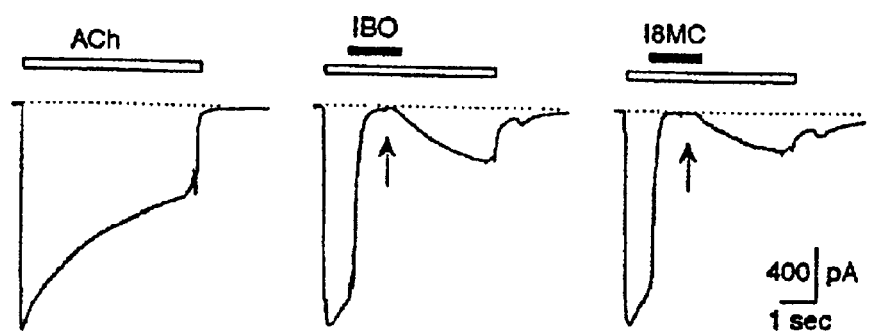
FIG. 1A is a graph of current vs. time showing whole-cell currents evoked by 1 mM ACh in transfected cells.

The present invention relates to a method for treating an addiction disorder in a patient. The method includes administering to the patient a first $\alpha_3\beta_4$ nicotinic receptor antagonist and administering to the patient a second $\alpha_3\beta_4$ nicotinic receptor antagonist.

As used herein, "addiction disorder" is meant to include a habitual or recurrent use of a substance, such as stimulants, nicotine (e.g., which is meant to include all forms of nicotine administration, such as smoking, chewing tobacco, or other forms of nicotine administration), opioid (e.g., morphine and heroin), amphetamines, cocaine, and alcohol. It is meant to include, but is not meant to be limited to, a dependency on the substance. Dependency is characterized by a patient's persistence in substance use or abuse or the recurrence of such use or abuse in the face of negative social or medical consequences of this use or abuse or in face of the patient's declared or undeclared intent to abandon or reduce his or her use of the substance. A patient's dependency can be manifested in objective criteria or other indices of drug seeking behavior, such as repeated attempts to abandon use or abuse of the substance, as evidenced by, for example, past participation in encounter groups designed to reduce the participants' use of cocaine or amphetamine, commitment to a drug or alcohol rehabilitation program, arrest or conviction of drug possession or trafficking, hospitalization for complications arising from drug or alcohol use, including overdose, and the like.

"Patient", as used herein, is generally meant to be a human. However, it is envisioned that the method of the present invention can be used to treat addiction disorders in experimental mammals other than humans, such as primates other than humans, rats, mice, dogs, and the like. Using the methods of the present invention, mammals experimentally addicted to drugs or alcohol can be humanely weaned from the substance, and the physiological and psychological damage or changes which result from past drug or alcohol use can be assessed. In addition, these mammals can be used to study the progression of or recovery from such physiological and psychological damage or changes subsequent to the patient's abandoning or reducing his, her, or its drug or alcohol use. In the controlled environment of the laboratory, the non-human mammalian patient would be allowed to develop drug or alcohol addiction and to maintain this addiction for a prescribed period of time. The patient's addiction would then be treated in accordance with the method of the present invention to cause the patient's use of the drug or alcohol to decrease or cease. The patient could then be monitored over time, e.g., from the time of the drug or alcohol use cessation or reduction to ascertain long-term physiological or psychological changes or damage and the patient's recovery from these changes or damage.

"$\alpha_3\beta_4$ nicotinic receptor antagonist", as used herein, means a compound that directly or indirectly blocks or otherwise reduces the activity of an $\alpha_3\beta_4$ nicotinic receptor. As used herein, "$\alpha_3\beta_4$ nicotinic receptor" is meant to include nicotinic receptors which contain three nicotinic receptor alpha subunits and four nicotinic receptor beta subunits, such as the $\alpha_3\beta_4$ nicotinic receptors described in Lucas et al. *Pharmacol. Rev.*, 51:397–401 (1999), which is hereby incorporated by reference. Nicotinic receptor alpha subunits are meant to include those described in GenBank Accession Nos. NM000743 (*Homo sapiens*) and X12434 (chicken), which are hereby incorporated by reference. Nicotinic receptor beta subunits are meant to include those described in GenBank Accession Nos. NM000750 (*Homo sapiens*) and U42976 (rat), which are hereby incorporated by reference. Examples of $\alpha_3\beta_4$ nicotinic receptor antagonists that are useful in the practice of the present invention include mecamylamine, 18-methoxycoronaridine (the preparation of which is described in Bandarage et al., *Tetrahedron*, 55:9405–9424 (1999), which is hereby incorporated by reference), bupropion (also known as m-chloro-α-tert-butylaminopropiophenone), dextromethorphan, and dextrorphan (which is a metabolite of dextromethorphan). Other examples of $\alpha_3\beta_4$ nicotinic receptor antagonists that are useful in the practice of the present invention include phamaceutically acceptable salts and solvates (the latter of which is meant to include adducts) of mecamylamine, 18-methoxycoronaridine, bupropion, dextromethorphan, and dextrorphan. Examples of suitable salts include those derived from inorganic bases (such as ammonium and alkali and alkaline earth metal hydroxides, carbonates, bicarbonates, and the like); salts derived from basic organic amines (such as aliphatic and aromatic amines, aliphatic diamines, hydroxy alkylamines, and the like), and salts derived from inorganic or organic acids, such as hydrochloric, hydrobromic, or hydroiodic acid). Bupropion hydrochloride and bupropion hydrobromide are but two examples of suitable pharmaceutically acceptable salts that can be used in the practice of the present invention. As used herein, "18-methoxycoronaridine" is meant to include the parent compound (i.e., 18-methoxycoronaridine per se) as well as 18-methoxycoronaridine congeners (e.g., the compounds represented by formula I in U.S. Pat. No. 6,211,360 to Glick et al., which is hereby incorporated by reference).

Suitable $\alpha_3\beta_4$ nicotinic receptor antagonists include those compounds which are selective for $\alpha_3\beta_4$ nicotinic receptors as well as those compounds which are not selective for $\alpha_3\beta_4$ nicotinic receptor. For the purposes of the present invention, a compound is to be deemed as being "selective for $\alpha_3\beta_4$ nicotinic receptors" if and only if the compound's $IC_{50}$ at an $\alpha_3\beta_4$ nicotinic receptor is less than (e.g., less than about 95% of, less than about 90% of, less than about 80% of, less than about 65% of, less than about 50% of, less than about 20% of, and/or less than about 10% of) the compound's $IC_{50}$ at an another nicotinic receptor (e.g., at the $\alpha_3\beta_4$ nicotinic receptor). In this regard, it should be noted that a compound's $IC_{50}$ at a nicotinic receptor can be measured or otherwise deduced using whole-cell patch-clamp methods, such as those described infra.

Suitable $\alpha_3\beta_4$ nicotinic receptor antagonists include those compounds which are specific for $\alpha_3\beta_4$ nicotinic receptors as well as those compounds which are not specific for $\alpha_3\beta_4$ nicotinic receptor. For the purposes of the present invention, a compound is to be deemed as being "specific for $\alpha_3\beta_4$ nicotinic receptors" if and only if the compound's $IC_{50}$ at an $\alpha_3\beta_4$ nicotinic receptor is less than about 20% of, less than about 15% of, less than about 10% of, less than about 8% of, less than about 5% of, and/or less than about 3% of) the compound's $IC_{50}$ at one other nicotinic receptor (e.g., at the $\alpha_3\beta_4$ nicotinic receptor), at more than one other (e.g., at two other) nicotinic receptor, or at all other nicotinic receptors. In this regard, it should again be noted that a compound's $IC_{50}$ at a nicotinic receptor can be measured or otherwise deduced using whole-cell patch-clamp methods, for example, as described infra.

As indicated above, the method of the present invention involves administering two different $\alpha_3\beta_4$ nicotinic receptor antagonists to the patient. For the purposes of the present invention, the first $\alpha_3\beta_4$ nicotinic receptor antagonist and the second $\alpha_3\beta_4$ nicotinic receptor antagonist are deemed to be "different" if they have different chemical formulae unless the first $\alpha_3\beta_4$ nicotinic receptor antagonist is a phamaceutically acceptable salt and/or solvate of the second $\alpha_3\beta_4$ nicotinic receptor or vice versa. For example, the first $\alpha_3\beta_4$ nicotinic receptor antagonist can be mecamylamine, 18-methoxycoronaridine, bupropion, dextromethorphan, or dextrorphan and the second $\alpha_3\beta_4$ nicotinic receptor antagonist can be a $\alpha_3\beta_4$ nicotinic receptor antagonist that is not selected from the group consisting of mecamylamine, 18-methoxycoronaridine, bupropion, dextromethorphan, and dextrorphan (or their pharmaceutically acceptable salts and/or solvates). Alternatively, both the first $\alpha_3\beta_4$ nicotinic receptor antagonist and the second $\alpha_3\beta_4$ nicotinic receptor antagonist can be selected from the group consisting of mecamylamine, 18-methoxycoronaridine, bupropion, dextromethorphan, dextrorphan, phamaceutically acceptable salts thereof, phamaceutically acceptable and solvates thereof, so long as the first and second $\alpha_3\beta_4$ nicotinic receptor antagonists are different from one another. Still alternatively, both the first and second $\alpha_3\beta_4$ nicotinic receptor antagonists can be $\alpha_3\beta_4$ nicotinic receptor antagonists that are not selected from the group consisting of mecamylamine, 18-methoxycoronaridine, bupropion, dextromethorphan, and dextrorphan (or their pharmaceutically acceptable salts and/or solvates).

Illustratively, the first $\alpha_3\beta_4$ nicotinic receptor antagonist can be mecamylamine and the second $\alpha_3\beta_4$ nicotinic receptor antagonist can be dextromethorphan. Alternatively, the first $\alpha_3\beta_4$ nicotinic receptor antagonist can be mecamylamine and the second $\alpha_3\beta_4$ nicotinic receptor antagonist can be dextrorphan. Still alternatively, the first $\alpha_3\beta_4$ nicotinic receptor antagonist can be mecamylamine and the second $\alpha_3\beta_4$ nicotinic receptor antagonist can be 18-methoxycoronaridine. Still alternatively, the first $\alpha_3\beta_4$ nicotinic receptor antagonist can be mecamylamine and the second $\alpha_3\beta_4$ nicotinic receptor antagonist can be a $\alpha_3\beta_4$ nicotinic receptor antagonist other than 18-methoxycoronaridine.

It is believed that each $\alpha_3\beta_4$ nicotinic receptor antagonist modulates not only the activity of the $\alpha_3\beta_4$ nicotinic receptor but also the activity of "other receptors". It is further believed that the "other receptors" that are modulated by a particular $\alpha_3\beta_4$ nicotinic receptor antagonist can vary depending on the nature of the particular $\alpha_3\beta_4$ nicotinic receptor antagonist. In the practice of the present invention, it is preferred that the $\alpha_3\beta_4$ nicotinic receptor antagonists be chosen such that the first $\alpha_3\beta_4$ nicotinic receptor antagonist modulates one set of "other receptors" and such that the second $\alpha_3\beta_4$ nicotinic receptor antagonist modulates another, different set of "other receptors". One set of "other receptors" is considered to be different from another set of "other receptors" if and only if there is not a one-to-one correspondence between the members of two sets of "other receptors".

Also as indicated above, the first and second $\alpha_3\beta_4$ nicotinic receptor antagonists can be administered simultaneously or non-simultaneously. Simultaneous administration is meant to include co-administration, as in the case where the two $\alpha_3\beta_4$ nicotinic receptor antagonists are administered as components of a single composition as well as in the case where the two $\alpha_3\beta_4$ nicotinic receptor antagonists are administered in separate compositions but at the same time (e.g., as two tablets swallowed simultaneously or as two solutions injected simultaneously). Non-simultaneous administration is meant to include sequential administration (e.g., in the case where the first $\alpha_3\beta_4$ nicotinic receptor antagonist is administered before the second or in the case where the second $\alpha_3\beta_4$ nicotinic receptor antagonist is administered before the first). When using sequential administration, it is preferred that the second-to-be-administered $\alpha_3\beta_4$ nicotinic receptor antagonist be administered while there is a substantial amount of the first-to-be-administered $\alpha_3\beta_4$ nicotinic receptor antagonist present in the patient. Generally, it is preferred to administer the second-to-be-administered $\alpha_3\beta_4$ nicotinic receptor antagonist within 3X, 2X, and/or 1X (where X is the first-to-be-administered $\alpha_3\beta_4$ nicotinic receptor antagonist metabolic half-life) of the time at which the first-to-be-administered $\alpha_3\beta_4$ nicotinic receptor antagonist was administered. For example, the second-to-be-administered $\alpha_3\beta_4$ nicotinic receptor antagonist can be administered to the patient within 4 hours, 3 hours, 2 hours, 1 hour, 30 minutes, 10 minutes, and/or 5 minutes of the time at which the first-to-be-administered $\alpha_3\beta_4$ nicotinic receptor antagonist was administered.

Preferably, the first and second $\alpha_3\beta_4$ nicotinic receptor antagonists are administered in amounts that are effective to treat the patient's addiction disorder. It will be appreciated that the actual preferred effective amount of first and second $\alpha_3\beta_4$ nicotinic receptor antagonists will vary according to the $\alpha_3\beta_4$ nicotinic receptor antagonists employed, the particular composition formulated, and the mode of administration. Many factors that modify the $\alpha_3\beta_4$ nicotinic receptor antagonists' activity will be taken into account by those skilled in the art; e.g., body weight, sex, diet, time of administration, route of administration, rate of excretion, condition of the patient, drug combinations, reaction sensitivities and severities, severity of addiction, and the stage at which the patient is in the withdrawal process. Administration of one or both of the $\alpha_3\beta_4$ nicotinic receptor antagonists can be carried out continuously or periodically within the maximum tolerated dose.

Illustratively, each $\alpha_3\beta_4$ nicotinic receptor antagonist can be administered in an amount from about 0.01 to about 10 mg/kg of the patient's body weight per day, for example, in an amount from about 0.02 to about 5 mg/kg of the patient's body weight per day or in an amount from about 0.1 to about 5 mg/kg of the patient's body weight per day. The optimal daily dose of each $\alpha_3\beta_4$ nicotinic receptor antagonist for a particular patient can be determined by challenging the patient with a dose of the substance to which they are addicted, the optimal daily dose of $\alpha_3\beta_4$ nicotinic receptor antagonist being the minimal dose at which the patient does not feel the effects of the challenge dose.

The amount of each $\alpha_3\beta_4$ nicotinic receptor antagonist can be administered in a single daily dose or in multiple doses or even continuously. Continuous administration can be carried out in the inpatient setting by, for example, intravenous drip, or in an outpatient setting by providing the $\alpha_3\beta_4$ nicotinic receptor antagonist(s) in a slow-release formulation, such as in a suspension or in microcapsules. In the outpatient setting, the administering is best carried out continuously in a slow release formulation, or, alternatively, in a single dose. In either case, to ensure compliance with the treatment protocol, it is best that the provider actively administer (i.e. inject, etc.) each individual dose to the patient or, instead, that the provider observe the patient self-administer each dose.

Each $\alpha_3\beta_4$ nicotinic receptor antagonist can be administered, individually or together, by any of the conventional modes of drug administration, including oral or parenteral administration. Examples of parenteral administration are intraventricular, intracerebral, intramuscular, intravenous, intraperitoneal, rectal, and subcutaneous administration.

Each $\alpha_3\beta_4$ nicotinic receptor antagonist or a composition containing the two can be administered alone or in combination with suitable pharmaceutical carriers or diluents. The diluent or carrier ingredients should be selected so that they do not diminish the therapeutic effects of the $\alpha_3\beta_4$ nicotinic receptor antagonists.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, microcapsules and the like. They may also be manufactured in the form of sterile solid compositions which can be dissolved or suspended in sterile injectable medium immediately before use. They may contain suspending or dispersing agents known in the art. Where microcapsules are employed, they can be readily prepared by conventional microencapsulation techniques, such as those disclosed in, for example, *Encyclopedia of Chemical Technology,* 3rd edition, volume 15, New York: John Wiley and Sons, pp. 470–493 (1981), which is hereby incorporated by reference.

The present invention, in another aspect thereof, relates to a composition which includes a first $\alpha_3\beta_4$ nicotinic receptor and a second $\alpha_3\beta_4$ nicotinic receptor, the second $\alpha_3\beta_4$ nicotinic receptor antagonist being different than the first $\alpha_3\beta_4$ nicotinic receptor antagonist. The meaning of "$\alpha_3\beta_4$ nicotinic receptor antagonist", examples of suitable nicotinic receptor antagonists, and methods for formulating these compositions are the same as set forth hereinabove. The optimal amounts of the first and the second $\alpha_3\beta_4$ nicotinic receptor antagonists present in the composition of the present invention can be determined from the optimal dosages as determined, for example, by using conventional dosage administration tests in view of the guidelines set forth above. Illustratively, the first and second $\alpha_3\beta_4$ nicotinic receptor antagonists can be present in a weight ratio of from about 10:1 to about 1:10, such as from about 5:1 to about 1:3, from about 3:1 to about 1:5, and/or from about 2:1 to about 1:2.

The present invention, in another aspect thereof, also relates to a method for treating an addiction disorder in a patient by administering to the patient an $\alpha_3\beta_4$ nicotinic receptor antagonist under conditions effective to treat the patient's addiction disorder.

Suitable $\alpha_3\beta_4$ nicotinic receptor antagonists useful in the practice of this aspect of the present invention include those which are not mecamylamine; are not 18-methoxycoronaridine; are not bupropion; are not dextromethorphan; are not dextrorphan, are not ibogaine; and are not a phamaceutically acceptable salt or solvate of mecamylamine, 18-methoxycoronaridine, bupropion, dextromethorphan, dextrorphan, or ibogaine. Additionally or alternatively, the $\alpha_3\beta_4$ nicotinic receptor antagonist can be selective and/or specific for $\alpha_3\beta_4$ nicotinic receptors. Other suitable $\alpha_3\beta_4$ nicotinic receptor antagonists useful in the practice of this aspect of the present invention include those which are more potent than 18-methoxycoronaridine at $\alpha_3\beta_4$ nicotinic receptors. For the purposes of the present invention, a compound is to be deemed as being "more potent than 18-methoxycoronaridine at $\alpha_3\beta_4$ nicotinic receptors" if and only if the compound's $IC_{50}$ at an $\alpha_3\beta_4$ nicotinic receptor is less than (e.g., less than about 95% of, less than about 95% of, less than about 80% of, less than about 65% of, less than about 50% of, less than about 20% of, and/or less than about 10% of) 18-methoxycoronaridine's $IC_{50}$ at the $\alpha_3\beta_4$ nicotinic receptor.

Suitable $\alpha_3\beta_4$ nicotinic receptor antagonists useful in the practice of this aspect of the present invention can be identified using conventional drug screening methodologies.

The present invention, in still another aspect thereof, relates to a method of evaluating a compound for its effectiveness in treating addiction disorders. The method includes assessing the compound's ability to bind to $\alpha_3\beta_4$ nicotinic receptors. For example, a test compound's ability to bind to $\alpha_3\beta_4$ nicotinic receptors (and hence its effectiveness in treating addiction disorders) can be assessed by providing an $\alpha_3\beta_4$ nicotinic receptor, contacting the test compound with the $\alpha_3\beta_4$ nicotinic receptor, and determining the amount of test compound which binds to the $\alpha_3\beta_4$ nicotinic receptor. The assessment can be carried out, for example, by using a conventional binding assay (e.g., a binding competition assay or an anssay which employs a labeled test compound), or it can be carried out by deducing the test compound's ability to bind to $\alpha_3\beta_4$ nicotinic receptors from whole-cell patch-clamp studies, such as those described infra. The assessment can also be carried out by reviewing data or other information, provided by others, regarding the compound's ability to bind to $\alpha_3\beta_4$ nicotinic receptors. The evaluation can also include other steps, such as administering the compound to patients suffering from addiction disorders and recording their progress, and/or administering the compound to patients suffering from addiction disorders recording any reported adverse side effects of the compound.

The present invention is further illustrated by the following examples.

EXAMPLES

Example 1

Receptor Functional Analyses

Human embryonic kidney 293 (HEK293) fibroblasts (ATCC CRL1573) were cultured in minimal essential medium supplemented with 10% fetal bovine serum and 2 mM glutamine (Life Technologies, Rockville, Md.). Cells were plated on poly-D-lysine-coated 35 mm nunc dishes, transfected by the LipofectaminePLUS method (Life Technologies), and examined functionally between 18–48 h post transfection. The following receptor subunit cDNAs were used: nAChR-$\alpha$3 (nicotinic acetylcholine receptor-$\alpha$3; accession no. L31621), nAChR-$\alpha$4 (accession no. L31620), nAChR-$\beta$2 (accession no. L31622), nAChR-$\beta$4 (accession no. U42976), 5-HT$_3$R-A (5-HT$_{3A}$ receptor; accession no. M74425), NR1 (N-methyl-D-aspartate receptor 1; accession no. X63255), NR2A (accession no. X91561), and NR2B (accession no. M91562). The nAchR and NR clones were rat; the 5-HT$_3$R-A clone was mouse. Co-transfection of enhanced green fluorescent protein ("EGFP") (10% of total cDNA) provided a marker to identify transfected cells. Transfected cells were selected for EGFP expression and examined by voltage-clamp recording in the whole-cell configuration using an Axopatch 200B patch-clamp amplifier (Axon Instruments, Foster City, Calif.). Thin-walled borosilicate glass microelectrodes (TW150F, World Precision Instruments, Sarasota, Fla.) had resistances of 3–5 M$\Omega$ when filled with an internal solution containing (in mM): 135 CsCl, 10 CsF, 10 HEPES (N-[2-hydroxyethyl] piperazine-N'-[2-ethanesulfonic acid]), 5 EGTA (ethylene glycol-bis[$\beta$-aminoethyl ether]-N,N,N',N'-tetraacetic acid), 1 MgCl$_2$, 0.5 CaCl$_2$, pH 7.2. Whole-cell capacitance and series resistance were recorded and adequately compensated using the available circuitry of the amplifier. Current responses were filtered at 1 kHz with an 8-pole Bessel filter (Cygnus Technologies, Delaware Water Gap, Pa.), digitized at 3 kHz, and stored on a Macintosh PowerPC-G3 computer using an ITC-16 interface (Instrutech, Great Neck, N.Y.) under control of the data acquisition and analysis program Synapse (Synergy Research, Gaithersburg, Md.). Cells were continuously superfused with extracellular solution containing (in mM): 150 NaCl, 3 KCl, 5 HEPES, 1 MgCl$_2$, 1.8 CaCl$_2$, 10 glucose, and 0.1 mg/ml phenol red, pH 7.3 (MgCl$_2$ was omitted from all solutions used for the study of NMDA receptors). Drug stocks (10 mM) were made up in dimethylsulfoxide ("DMSO") and diluted in extracellular solution immediately prior to use; final concentration of DMSO was 0.2% or lower. Control, agonist, and drug solutions were applied to individual cells by rapid perfusion. Solutions were driven by a syringe pump through a flowpipe having 4 inputs that converge at a single common output of approximately 100 $\mu$m diameter. Rapid switching between inputs was achieved using a set of upstream solenoid valves (Lee Co., Westbrook, Conn.) under computer control; the solution exchange rate was ~5 ms as measured from liquid junction currents.

Example 2

Chemicals and Animals

18-Methoxycoronaridine hydrochloride (1–2 mg/kg; Albany Molecular Research, Inc., Albany, N.Y.) was dissolved in phosphate buffer and injected intraperitoneally 15 minutes before behavioral testing. Dextromethorphan hydrobromide (5 mg/kg; Sigma/RBI, St. Louis, Mo.) was dissolved in saline and injected subcutaneously 20 minutes before testing. Mecamylamine hydrochloride (1 mg/kg; Sigma/RBI, St. Louis, Mo.) was dissolved in physiological saline and injected intraperitoneally 30 minutes before testing. All rats received two injections. For rats that received a single drug, half of them also received the appropriate saline/vehicle injection corresponding to each of the other two drugs.

Naive female Long-Evans derived rats (250 g; Charles River, N.Y.) were maintained on a normal 12 h light cycle (lights on at 7:00 a.m., lights off at 7:00 p.m.). For all experiments the "Principles of Laboratory Animal Care" (NIH publication No. 85-23, revised 1985, which is hereby incorporated by reference) were followed.

Example 3

Self-administration Procedure

The intravenous self-administration procedure described in Glick et al., "18-MC Reduces Methamphetamine and Nicotine Self-administration in Rats," *NeuroReport* 11:2013–2015 (2000) ("Glick I"), which is hereby incorporated by reference, was employed. Briefly, responses on either of two levers (mounted 15 cm apart on the front wall of each operant test cage) were recorded on an IBM compatible computer with a Med Associates, Inc. interface. The intravenous self-administration system consisted of polyethylene-silicone cannulas constructed according to the design of Weeks, "Long-term Intravenous Infusion," pp. 155–168 in Myers (ed.), *Methods in Psychobiology*, Vol. 2, New York: Academic Press (1972) ("Weeks"), which is hereby incorporated by reference; Instech harnesses and swivels; and Harvard Apparatus infusion pumps (#55-2222). Shaping of the bar-press response was initially accomplished by training rats to bar-press for water. Cannulas were then implanted in the external jugular vein according to procedures described in Weeks, which is hereby incorporated by reference. Self-administration testing began with a 16-h nocturnal session followed by daily 1-h sessions, 5 days (Monday-Friday) a week. A lever-press response produced a 10 µl infusion of drug solution (0.01 mg of morphine sulfate) in about 0.2 s or a 50 µl infusion of drug solution (0.025 mg of methamphetamine sulfate) in about 1 s. Since all rats generally weighed 250±20 g, each response delivered approximately 0.04 mg/kg of morphine or 0.1 mg/kg of methamphetamine. Experiments to assess the effects of experimental treatments were begun when baseline self-administration rates stabilized ($\leq$10% variation from one day to the next across 5 days), usually after 2 weeks of testing. Each rat typically received two or three different treatments spaced at least one week apart. In order to provide an indication of the specificity of treatment effects on drug self-administration, all treatments were also administered to other rats bar-pressing for water (0.01 ml orally) on a comparable schedule (continuous reinforcement; 1-h sessions).

Example 4

Drug Actions at Neurotransmitter Receptor Ion-channels

Figure 1B:
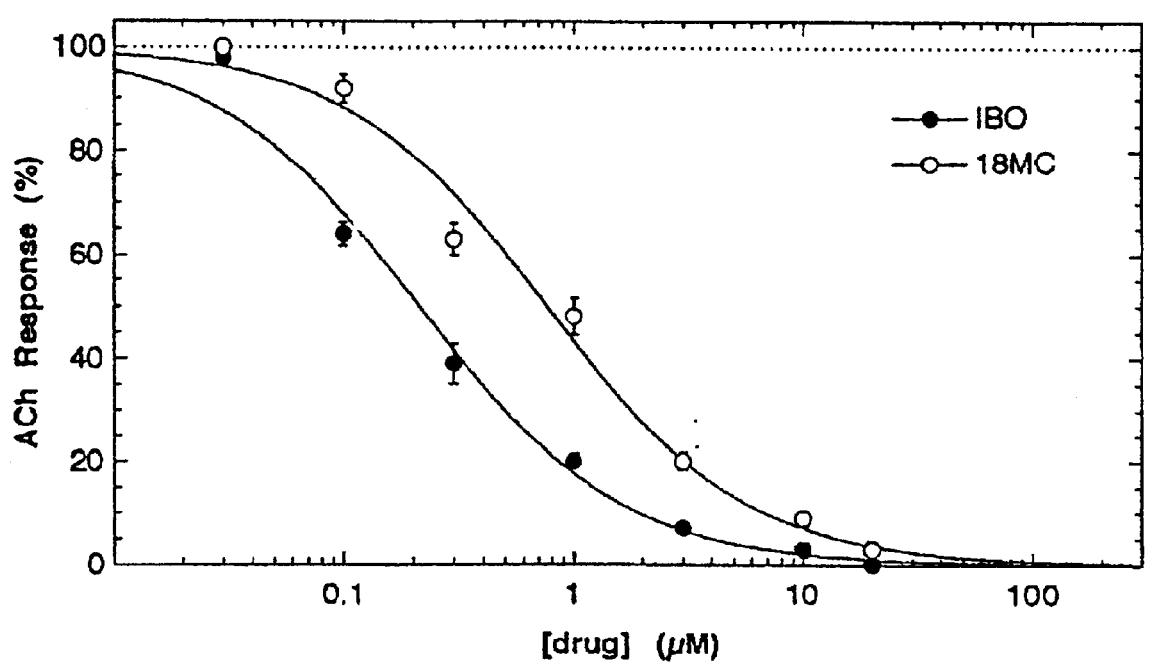
FIG. 1B is a graph showing inhibition of 1 mM ACh-evoked whole-cell currents by various concentrations of various drugs.
Figure 2:
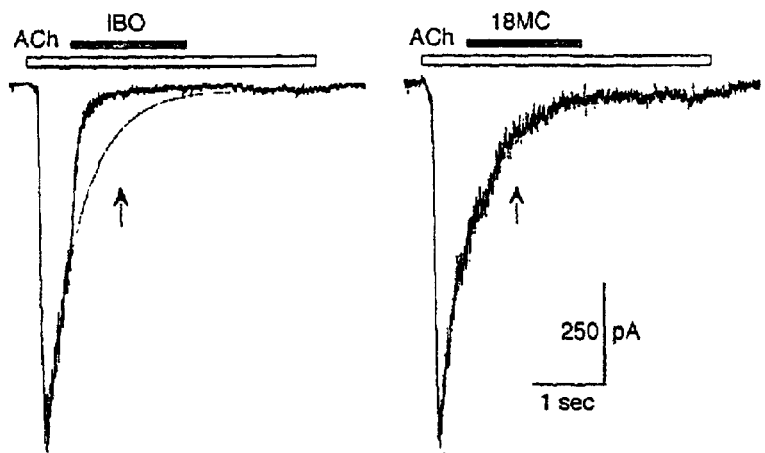
FIG. 2 is a graph of whole-cell current vs. time showing the effect of various drugs on whole-cell currents in cells expressing recombinant $\alpha_3\beta_4$ nicotinic receptors.

Transfected HEK293 cells expressing various receptor subunit cDNAs were examined by whole-cell patch-clamp recording with fast perfusion of agonist and drug solutions. We began with $\alpha_3\beta_4$ nACh receptors as these are the principal ganglionic nACh receptor subtype for which inhibition by ibogaine had previously been demonstrated (Badio et al., "Ibogaine: A Potent Noncompetitive Blocker of Ganglionic/Neuronal Nicotinic Receptors," *Molec. Pharmacol.*, 51:1–5 (1997); Mah et al., "Ibogaine Acts at the Nicotinic Acetylcholine Receptor to Inhibit Catecholamine Release," *Brain Res.*, 797:173–180 (1998); and Fryer et al., "Noncompetitive Functional Inhibition at Diverse, Human Nicotinic Acetylcholine Receptor Subtypes by Bupropion, Phencyclidine, and Ibogaine," *J. Pharmacol. Exp. Ther.*, 288:88–92 (1999), which are hereby incorporated by reference). Transfected HEK293 cells expressing $\alpha_3\beta_4$ nACh receptors were voltage-clamped to –70 mV and stimulated with 1 mM ACh at 30 s intervals. ACh alone evoked a large inward current not seen in untransfected cells. Application of 20 µM ibogaine or 20 µM 18-methoxycoronaridine alone did not produce any response. As shown in FIG. 1A, co-application of either 20 µM ibogaine ("IBO") or 20 µM 18-methoxycoronaridine ("18MC") nearly abolished the ACh-evoked responses in all cells tested (N=15). In FIG. 1A, open bars depict the timing of ACh application; filled bars depict the timing of co-application of 20 µM IBO or 20 µM 18MC; and inhibition was measured relative to control at the end of the drug application (indicated by arrows). The inhibition developed rapidly in the presence of ACh and reversed more slowly following the removal of drug. As shown in FIG. 1B, the inhibition was concentration-dependent; $IC_{50}$ values were 0.22 µM for ibogaine versus 0.75 µM for 18-methoxycoronaridine, and the concentration-response relationship had a Hill slope of unity which is consistent with a single site of action. More particularly, FIG. 1B shows the inhibition of 1 mM ACh-evoked currents by various concentrations of IBO and 18MC. The data presented in FIG. 1B are mean±SEM for 3–14 cells per point, and curve fits are given for the logistic equation: $I=I_{max}/(1+([drug]/IC_{50}))$. Best fitting $IC_{50}$ values were 0.75 µM for IBO and 0.22 µM for 18MC. These data confirm previous reports of the actions of ibogaine and indicate that 18-methoxycoronaridine has similar actions at ganglionic nACh receptors. Results were somewhat different, however, at neuronal nACh receptors. In this case, transfected HEK293 cells expressing $\alpha_3\beta_4$ nACh receptors were voltage-clamped to –70 mV and stimulated with 300 µM ACh at 30 s intervals. ACh alone evoked an inward current whereas application of 20 µM ibogaine or 20 µM 18-methoxycoronaridine alone did not produce any response. Co-application of 5 µM ibogaine inhibited the ACh-evoked response by 61±4% (n=5) whereas 5 µM 18-methoxycoronaridine produced no apparent inhibition (N=6). This is shown in FIG. 2, where open bars depict the timing of ACh application and filled bars depict the timing of co-application of 20 µM IBO or 20 µM 18MC. Because of the relatively rapid desensitization of the $\alpha_3\beta_4$ response, inhibition was measured relative to control (superimposed curve fits) during drug application (arrows). At higher drug concentrations (20 µM), ibogaine inhibition reached 93±3% (N=7) versus only 8 ±4% by 18-methoxycoronaridine (N=6). These data suggest the $IC_{50}$ for ibogaine at $\alpha_3\beta_4$ nACh receptors is on the order of 1–5 $\mu$M and that 18-methoxycoronaridine is considerably less potent (IC$_{50}$>20 $\mu$M) at this neuronal nACh receptor subtype.

Figure 3A:
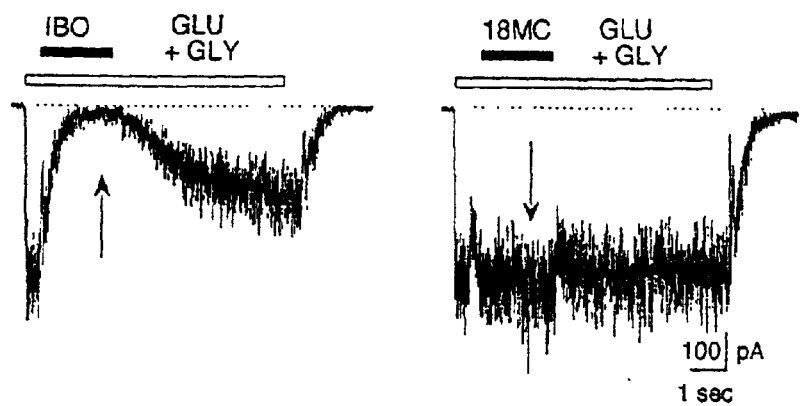
FIGS. 3A and 3B are graphs of whole-cell current vs. time showing the effect of various drugs on whole-cell currents in cells expressing recombinant NR1/2A (FIG. 3A) and NR1/2B (FIG. 3B) receptors.
Figure 3B:
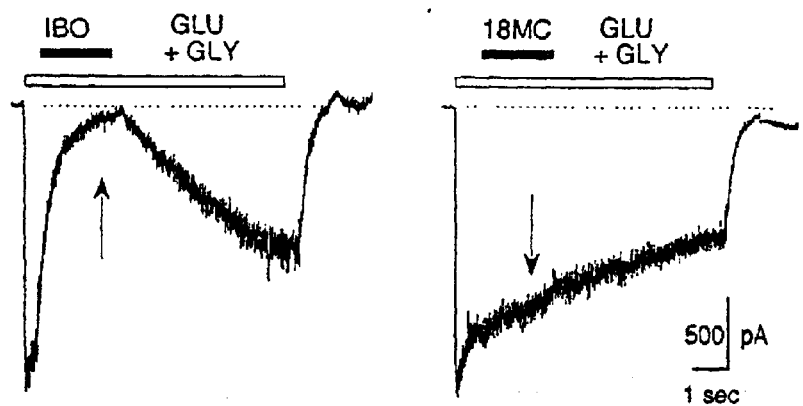

Another known action of ibogaine involves the inhibition of NMDA-type glutamate receptors (Popik et al., "NMDA Antagonist Properties of the Putative Antiaddictive Drug, Ibogaine," *J. Pharmacol. Exp. Ther.,* 275:753–760 (1995) ("Popik") and Chen et al., "Ibogaine Block of the NMDA Receptor: In Vitro and In Vivo Studies," *Neuropharmacology,* 35:423–431 (1996) ("Chen"), which are hereby incorporated by reference), presumably by interaction with the PCP/MK-801 (phencyclidine/dizocilpine) binding site (Sweetnam et al., "Receptor Binding Profile Suggests Multiple Mechanisms of Action Are Responsible for Ibogaine's Putative Anti-addictive Activity," *Psychopharmacoloqy,* 118:369–376 (1995) ("Sweetnam") and Chen, which are hereby incorporated by reference). Indeed, it has been suggested that the NMDA receptor-mediated actions of ibogaine may be central to its putative anti-addictive properties (Popik, which is hereby incorporated by reference). To study these, transfected HEK293 cells expressing NR1/2A or NR1/2B receptors were voltage-clamped to −70 mV and stimulated with 100 $\mu$M glutamate plus 10 $\mu$M glycine at 30 s intervals. Agonist application evoked a large inward current not seen in untransfected cells. Application of 20 $\mu$M ibogaine or 20 $\mu$M 18-methoxycoronaridine alone did not produce any response. Co-application of 20 $\mu$M ibogaine reduced the agonist-evoked response of NR1/2A receptors by 98±3% (N=3) and of NR1/2B receptors by 95±2% (N=3); inhibition by 10 $\mu$M ibogaine was 51±9% (n=3) and 82±3% (n=3), respectively. These data are consistent with IC$_{50}$ values of 3–5 $\mu$M obtained in hippocampal neurons (Popik and Chen, which are hereby incorporated by reference). However, as shown in FIGS. 3A and 3B, we also found that co-application of 18-methoxycoronaridine failed to inhibit either NR1/2A (N=3) (FIG. 3A) or NR1/2B receptors (N=5) (FIG. 3B) at concentrations up to 20 $\mu$M. In FIGS. 3A and 3B, open bars depict the timing of agonist application, filled bars depict the timing of co-application of 20 $\mu$M IBO or 20 $\mu$M 18MC, and inhibition was measured relative to control at the end of the drug application (indicated by arrows). This result necessarily calls into question any role of NMDA receptors in the putative anti-addictive actions of these drugs.

Figure 4:
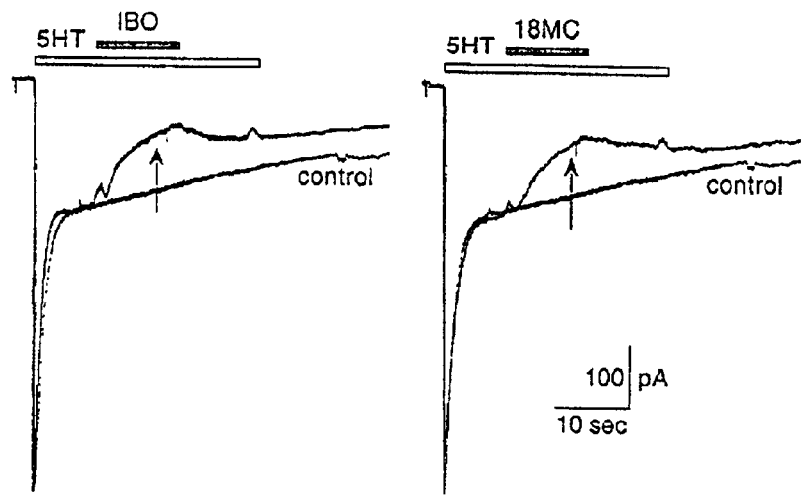
FIG. 4 is a graph of whole-cell current vs. time showing the effect of various drugs on whole-cell currents in cells expressing recombinant 5-HT$_3$ receptors.

There are no published studies examining the effects of ibogaine on 5-HT$_3$ receptor function. Although some action may be expected based on competition binding studies (Sweetnam, which is hereby incorporated by reference), it remains to be seen whether ibogaine binding to these receptors activates, inhibits, or otherwise alters channel function. Likewise, the effects of 18-methoxycoronaridine on 5-HT$_3$ receptor function have not been examined. Transfected HEK293 cells expressing 5-HT$_{3A}$ receptors were voltage-clamped to −70 mV and stimulated with 100 $\mu$M serotonin at 30 s intervals. Serotonin alone evoked an inward current not seen in untransfected cells. Application of 20 $\mu$M ibogaine or 20 $\mu$M 18-methoxycoronaridine alone did not produce any response, indicating that neither is an agonist at 5-HT, receptors. Co-application of 20 $\mu$M ibogaine or 20 $\mu$M 18-methoxycoronaridine inhibited serotonin-evoked responses by 53±3% (N=8) versus 50±3% (N=4), respectively. This is shown in FIG. 4, where open bars depict the timing of agonist application, filled bars depict the timing of co-application of 20 $\mu$M IBO or 20 $\mu$M 18MC, and inhibition was measured relative to control at the end of the drug application (indicated by arrows). Thus, it appears that these drugs have similar potencies at 5-HT$_3$ receptors with IC$_{50}$ values of approximately 20 $\mu$M.

Example 5

Figure 5:
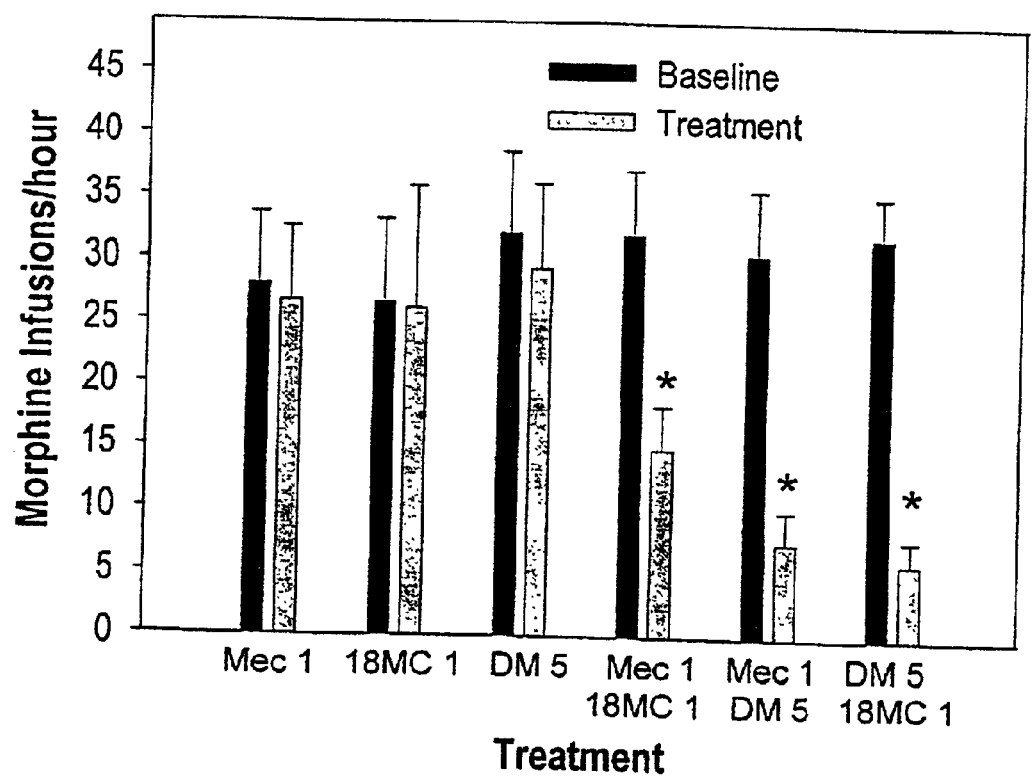
FIG. 5 is a bar graph showing the effects of various drugs and drug combinations on morphine self-administration.
Figure 6:
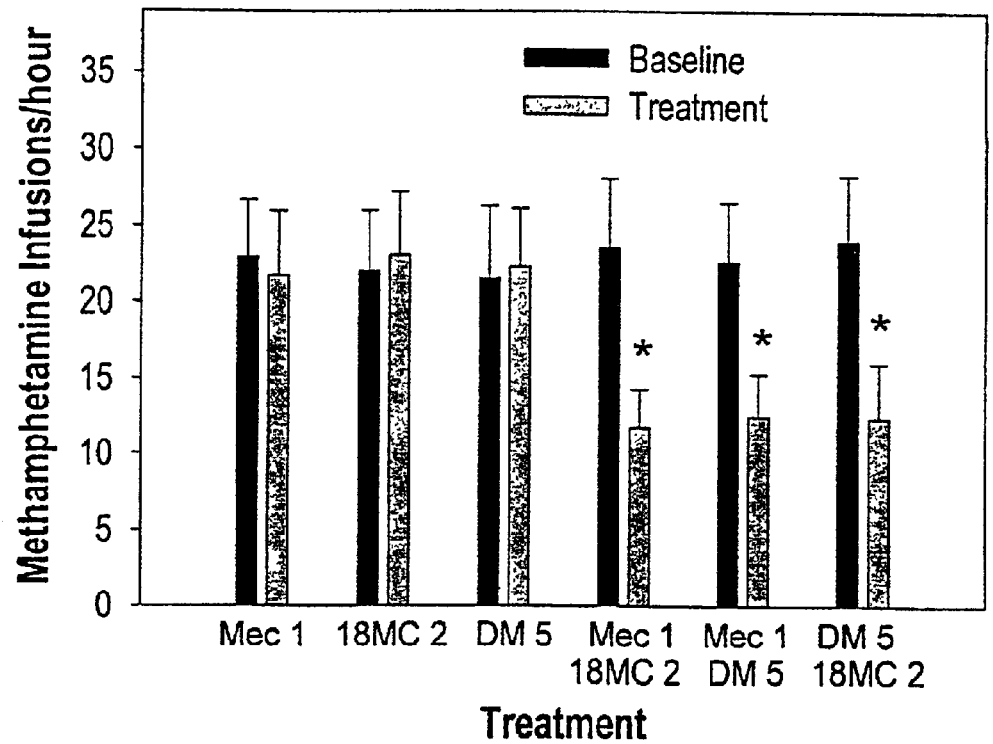
FIG. 6 is a bar graph showing the effects of various drugs and drug combinations on methamphetamine self-administration.
Figure 7:
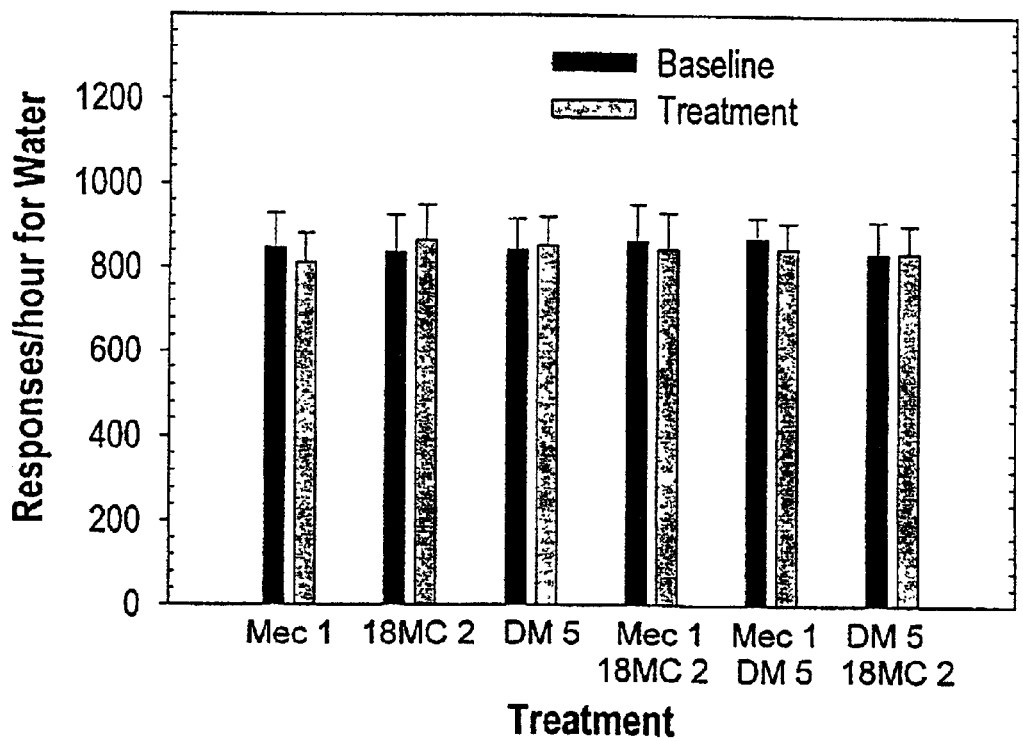
FIG. 7 is a bar graph showing the effects of various drugs and drug combinations on responding for water.

Effect of Mecamylamine, 18-Methoxycoronaridine, Dextromethorphan, Mecamylamine/18-Methoxycoronaridine, Mecamylamine/Dextromethorphan, and Dextromethorphan/18-Methoxycoronaridine Drug Treatments on Morphine and Methamphetamine Self-administration FIGS. 5–7 show the effects of mecamylamine, 18-methoxycoronaridine, dextromethorphan, mecamylamine/18-methoxycoronaridine, mecamylamine/dextromethorphan, and dextromethorphan/18-methoxycoronaridine drug treatments on morphine and methamphetamine self-administration and on responding for water.

More particularly, FIG. 5 shows the effects of the drugs and drug combinations on morphine self-administration. Rats were administered two of the following treatments before testing: mecamylamine (1 mg/kg i.p., 30 min) ("Mec 1"), 18-methoxycoronaridine (1 mg/kg i.p., 15 min) ("18MC 1"), dextromethorphan (5 mg/kg s.c., 20 min) ("DM 5"), or vehicle (saline for mecamylamine and dextromethorphan; phosphate buffer for 18-methoxycoronaridine). Each data point represents the mean (±S.E.M.) percent of baseline of 6–8 rats. Significant differences between baseline and treatment are indicated by an asterisk (paired t-test, P<0.01–0.001).

FIG. 6 shows the effects of the drugs and drug combinations on methamphetamine self-administration. Rats were administered two of the following treatments before testing: mecamylamine (1 mg/kg i.p., 30 min) ("Mec 1"), 18-methoxycoronaridine (2 mg/kg i.p., 15 min) ("18MC 2"), dextromethorphan (5 mg/kg s.c., 20 min) ("DM 5"), or vehicle (saline for mecamylamine and dextromethorphan; phosphate buffer for 18-methoxycoronaridine). Each data point represents the mean (±S.E.M.) percent of baseline of 6–7 rats. Significant differences between baseline and treatment are indicated by an asterisk (paired t-test, P<0.01).

FIG. 7 shows the effects of the drugs and drug combinations on responding for water. Rats were administered two of the following treatments before testing: mecamylamine (1 mg/kg i.p., 30 min) ("Mec 1"), 18-methoxycoronaridine (2 mg/kg i.p., 15 min) ("18MC 2"), dextromethorphan (5 mg/kg s.c., 20 min) ("DM 5"), or vehicle (saline for mecamylamine and dextromethorphan; phosphate buffer for 18-methoxycoronaridine). Each data point represents the mean (±S.E.M.) percent of baseline of 6 rats.

All three drug combinations (i.e., mecamylamine/18-methoxycoronaridine, mecamylamine/dextromethorphan, and dextromethorphan/18-methoxycoronaridine), but none of the drugs administered alone, significantly decreased morphine and methamphetamine self-administration while having no effect on responding for water. The particular doses of 18-methoxycoronaridine, dextromethorphan, and mecamylamine selected for study were, in each instance, based on the respective dose-response functions. The doses of 18-methoxycoronaridine (1 and 2 mg/kg) were approximately one-fifth of those required to decrease morphine (Glick et al., "18-Methoxycoronaridine, a Non-toxic Iboga Alkaloid Congener: Effects on Morphine and Cocaine Self-administration and on Mesolimbic Dopamine Release in Rats," *Brain Res.,* 719:29–35 (1996), which is hereby incorporated by reference) and methamphetamine (Glick I, which is hereby incorporated by reference) self-administration, respectively, when administered alone. The dose of dextromethorphan (5 mg/kg) was one-half to one-fourth of that necessary to decrease morphine and methamphetamine self-administration (Glick et al., "Comparative Effects of Dextromethorphan and Dextrorphan on Morphine, Methamphetamine, and Nicotine Self-administration in Rats," *Europ. J. Pharmacol.*, 422:87–90 (2001), which is hereby incorporated by reference), respectively, when administered alone. The dose of mecamylamine (1 mg/kg) was one-third of that required to decrease either morphine or methamphetamine self-administration, and, at a dose of 3 mg/kg, mecamylamine also decreases responding for water (data not shown). Lastly, although FIG. 7 only shows results with the 2 mg/kg dosage of 18-methoxycoronaridine, virtually identical results were found with 1 mg/kg.

Example 6

Figure 8:
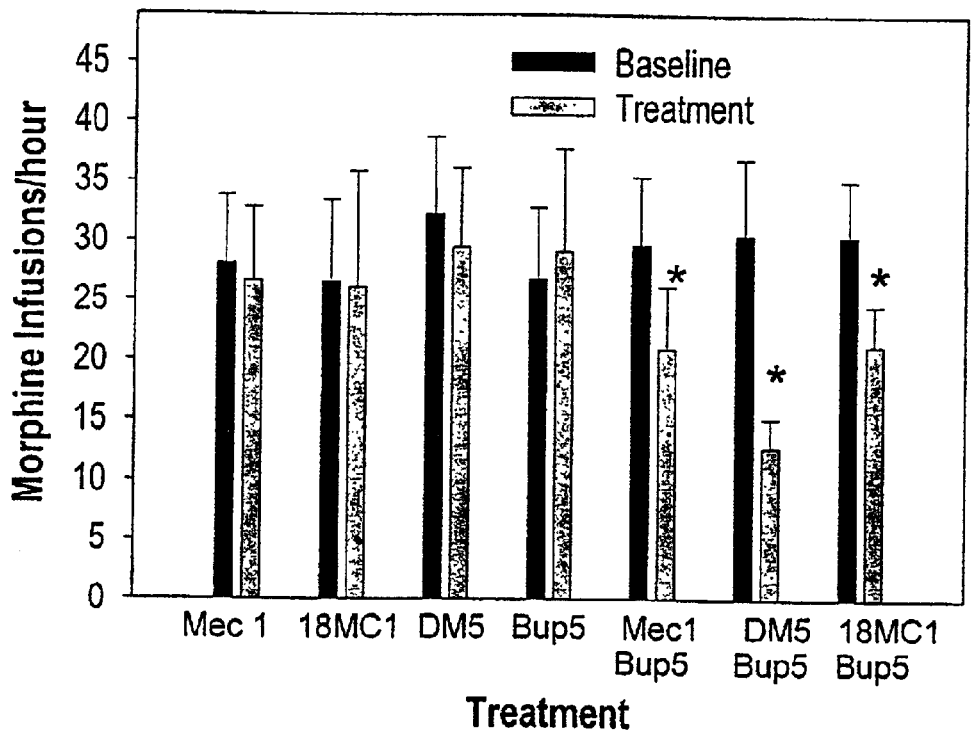
FIG. 8 is a bar graph showing the effects of various drugs and drug combinations on morphine self-administration.
Figure 9:
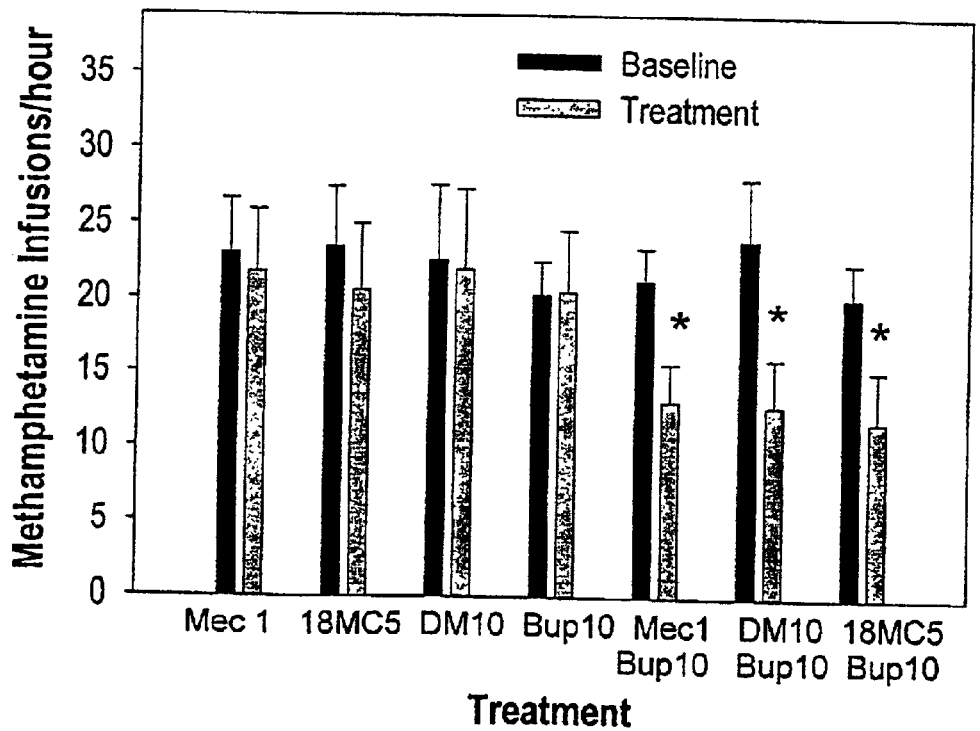
FIG. 9 is a bar graph showing the effects of various drugs and drug combinations on methamphetamine self-administration.
Figure 10:
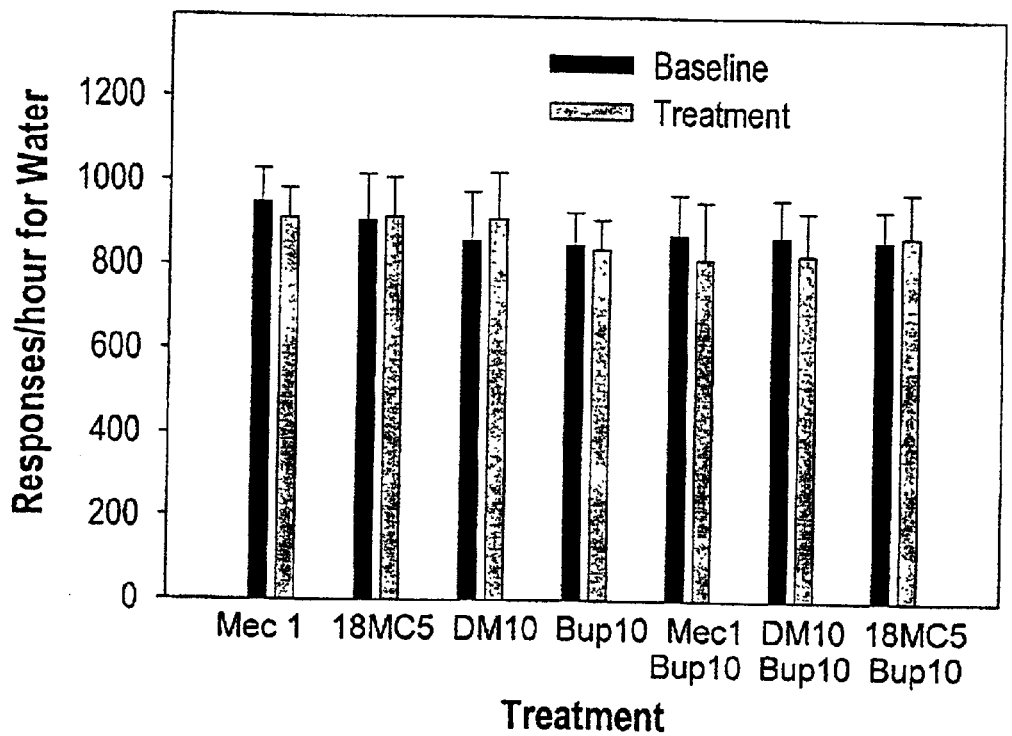
FIG. 10 is a bar graph showing the effects of various drugs and drug combinations on responding for water.

Effect of Mecamylamine, 18-Methoxycoronaridine, Dextromethorphan, Bupropion, Mecamylamine/Bupropion, Dextromethorphan/Bupropion, and 18-Methoxycoronaridine/Bupropion Drug Treatments on Morphine and Methamphetamine Self-administration FIGS. 8–10 show the effects of mecamylamine, 18-methoxycoronaridine, dextromethorphan, bupropion, mecamylamine/bupropion, dextromethorphan/bupropion, and 18-methoxycoronaridine/bupropion drug treatments on morphine and methamphetamine self-administration and on responding for water.

More particularly, FIG. 8 shows the effects of the drugs and drug combinations on morphine self-administration. Rats were administered two of the following treatments before testing: mecamylamine (1 mg/kg i.p., 30 min) ("Mec 1"), 18-methoxycoronaridine (1 mg/kg i.p., 15 min) ("18MC1"), dextromethorphan (5 mg/kg s.c., 20 min) ("DM5"), bupropion (5 mg/kg i.p., 15 min) ("Bup5"), or vehicle (saline for mecamylamine, dextromethorphan and bupropion; phosphate buffer for 18-methoxycoronaridine). Each data point represents the mean (±S.E.M.) percent of baseline of 5–8 rats. Significant differences between baseline and treatment are indicated by an asterisk (paired t-test), P<0.05–0.01).

FIG. 9 shows the effects of the drugs and drug combinations on methamphetamine self-administration. Rats were administered two of the following treatments before testing: mecamylamine (1 mg/kg i.p., 30 min) ("Mec 1"), 18-methoxycoronaridine (5 mg/kg i.p., 15 min) ("18MC5"), dextromethorphan (10 mg/kg s.c., 20 min) ("DM10"), bupropion (10 mg/kg i.p., 15 min) ("Bup10"), or vehicle (saline for mecamylamine, dextromethorphan and bupropion; phosphate buffer for 18-methoxycoronaridine). Each data point represents the mean (±S.E.M.) percent of baseline of 5–9 rats. Significant differences between baseline and treatment are indicated by an asterisk (paired t-test, P<0.01).

FIG. 10 shows the effects of the drugs and drug combinations on responding for water. Rats were administered two of the following treatments before testing: mecamylamine (1 mg/kg i.p., 30 min) ("Mec 1"), 18-methoxycoronaridine (5 mg/kg i.p., 15 min) ("18MC5"), dextromethorphan (10 mg/kg s.c., 20 min) ("DM10"), bupropion (10 mg/kg i.p., 15 min) ("Bup10"), or vehicle (saline for mecamylamine, dextromethorphan and bupropion; phosphate buffer for 18-methoxycoronaridine). Each data point represents the mean (±S.E.M.) percent of baseline of 6–7 rats.

All three drug combinations (i.e., mecamylamine/bupropion, dextromethorphan/bupropion, and 18-methoxycoronaridine/bupropion), but none of the drugs administered alone, significantly decreased morphine and methamphetamine self-administration while having no effect on responding for water.

Example 7

Effect of Drugs and Drug Combinations on Nicotine Self-administration

Figure 11:
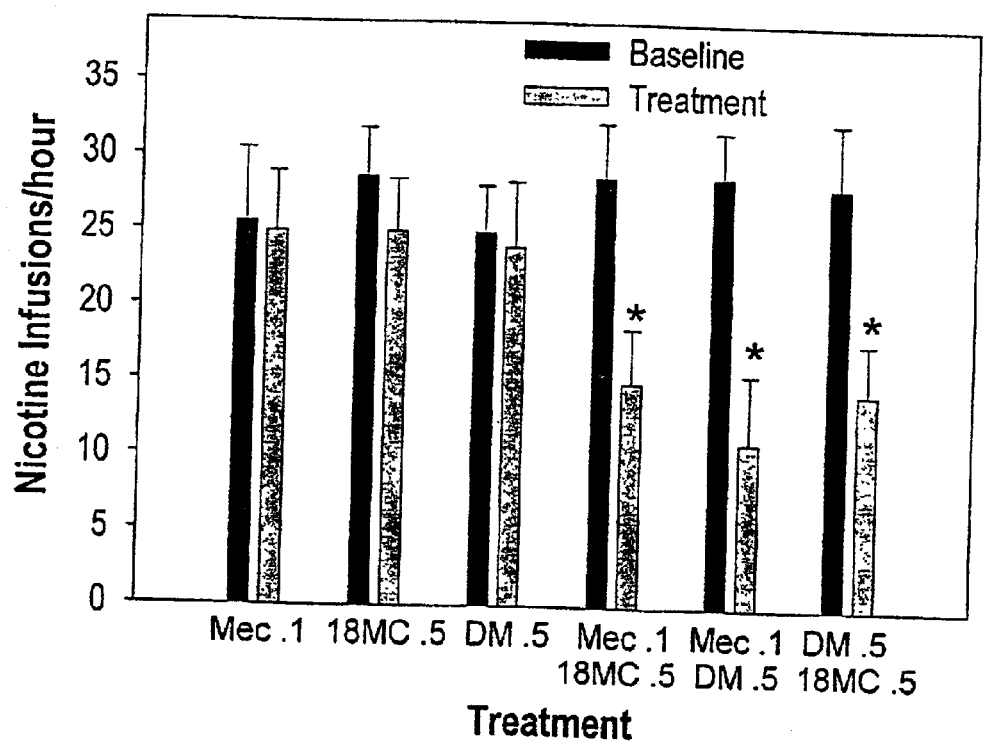
FIG. 11 is a bar graph showing the effects of various drugs and drug combinations on nicotine self-administration.

FIGS. 11 and 12 show the effects of mecamylamine, 18-methoxycoronaridine, dextromethorphan, bupropion, mecamylamine/18-methoxycoronaridine, mecamylamine/dextromethorphan, and dextromethorphan/18-methoxycoronaridine, mecamylamine/bupropion, dextromethorphan/bupropion, and 18-methoxycoronaridine/bupropion drug treatments on nicotine self-administration.

More particularly, FIG. 11 shows the effects of mecamylamine, 18-methoxycoronaridine, dextromethorphan, mecamylamine/18-methoxycoronaridine, mecamylamine/dextromethorphan, and dextromethorphan/18-methoxycoronaridine, on nicotine self-administration. Rats were administered two of the following treatments before testing: mecamylamine (0.1 mg/kg i.p., 30 min) ("Mec 0.1"), 18-methoxycoronaridine (0.5 mg/kg i.p., 15 min) ("18MC 0.5"), dextromethorphan (0.5 mg/kg s.c., 20 min) ("DM 0.5"), or vehicle (saline for mecamylamine and dextromethorphan; phosphate buffer for 18-methoxycoronaridine). Each data point represents the mean (±S.E.M.) percent of baseline of 5–7 rats. Significant differences between baseline and treatment are indicated by an asterisk (paired t-test, P<0.01).

FIG. 12 shows the effects of mecamylamine, 18-methoxycoronaridine, dextromethorphan, bupropion, mecamylamine/bupropion, dextromethorphan/bupropion, and 18-methoxycoronaridine/bupropion drug treatments on nicotine self-administration. Rats were administered two of the following treatments before testing: mecamylamine (0.1 mg/kg i.p., 30 min) ("Mec 0.1"), 18-methoxycoronaridine (0.5 mg/kg i.p., 15 min) ("18MC 0.5"), dextromethorphan (0.5 mg/kg s.c., 20 min) ("DM 0.5"), bupropion (5 mg/kg i.p., 15 min) ("Bup5"), or vehicle (saline for mecamylamine, dextromethorphan and bupropion; phosphate buffer for 18-methoxycoronaridine). Each data point represents the mean (±S.E.M.) percent of baseline of 5–8 rats. Significant differences between baseline and treatment are indicated by an asterisk (paired t-test, P<0.01).

All six drug combinations (i.e., mecamylamine/18-methoxycoronaridine, mecamylamine/dextromethorphan, dextromethorphan/18-methoxycoronaridine, mecamylamine/bupropion, dextromethorphan/bupropion, and 18-methoxycoronaridine/bupropion), but none of the drugs administered alone, significantly decreased nicotine self-administration. Control experiments showed that these drug combinations had no significant effect on responding for water.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A composition comprising a first $\alpha_3\beta_4$ nicotinic receptor antagonist and a second $\alpha_3\beta_4$ nicotinic receptor antagonist, wherein said first $\alpha_3\beta_4$ nicotinic receptor antagonist is 18-methoxycoronaridine or a pharmaceutically acceptable salt or solvate thereof and said second $\alpha_3\beta_4$ nicotinic receptor antagonist is mecamylamine or a pharmaceutically acceptable salt or solvate thereof.

2. A composition according to claim 1, wherein said first $\alpha_3\beta_4$ nicotinic receptor antagonist and said second $\alpha_3\beta_4$ nicotinic receptor antagonist are present in a weight ratio of from about 10:1 to about 1:10.

3. A composition according to claim 1, wherein said first $\alpha_3\beta_4$ nicotinic receptor antagonist and said second $\alpha_3\beta_4$ nicotinic receptor antagonist are present in a weight ratio of from about 5:1 to about 1:5.

4. A composition according to claim 1, wherein said composition is in the form of a tablet, capsule, granular dispersible powder, suspension, syrup, or elixir.

5. A composition according to claim 1, wherein said composition is in the form of a tablet or capsule and wherein said composition further comprises an inert diluent, a granulating agent, a disintegrating agent, a lubricating agent, or combinations thereof.

6. A method for treating nicotine addiction in a patient, said method comprising: administering to the patient a composition according to claim 1.

7. A method according to claim 6, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

8. A method according to claim 6, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

9. A method for treating amphetamine addiction in a patient, said method comprising: administering to the patient a composition according to claim 1.

10. A method according to claim 9, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

11. A method according to claim 9, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

12. A method for treating opioid addiction in a patient, said method comprising: administering to the patient a composition according to claim 1.

13. A method according to claim 12, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

14. A method according to claim 12, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

15. A composition comprising a first $\alpha_3\beta_4$ nicotinic receptor antagonist and a second $\alpha_3\beta_4$ nicotinic receptor antagonist, wherein said first $\alpha_3\beta_4$ nicotinic receptor antagonist is 18-methoxycoronaridine or a pharmaceutically acceptable salt or solvate thereof and said second $\alpha_3\beta_4$ nicotinic receptor antagonist is dextromethorphan or a pharmaceutically acceptable salt or solvate thereof.

16. A composition according to claim 15, wherein said first $\alpha_3\beta_4$ nicotinic receptor antagonist and said second $\alpha_3\beta_4$ nicotinic receptor antagonist are present in a weight ratio of from about 10:1 to about 1:10.

17. A composition according to claim 15, wherein said first $\alpha_3\beta_4$ nicotinic receptor antagonist and said second $\alpha_3\beta_4$ nicotinic receptor antagonist are present in a weight ratio of from about 5:1 to about 1:5.

18. A composition according to claim 15, wherein said composition is in the form of a tablet, capsule, granular dispersible powder, suspension, syrup, or elixir.

19. A composition according to claim 15, wherein said composition is in the form of a tablet or capsule and wherein said composition further comprises an inert diluent, a granulating agent, a disintegrating agent, a lubricating agent, or combinations thereof.

20. A method for treating nicotine addiction in a patient, said method comprising: administering to the patient a composition according to claim 15.

21. A method according to claim 20, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

22. A method according to claim 20, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

23. A method for treating amphetamine addiction in a patient, said method comprising: administering to the patient a composition according to claim 15.

24. A method according to claim 23, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

25. A method according to claim 23, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

26. A method for treating opioid addiction in a patient, said method comprising: administering to the patient a composition according to claim 15.

27. A method according to claim 25, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

28. A method according to claim 26, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

29. A composition comprising a first $\alpha_3\beta_4$ nicotinic receptor antagonist and a second $\alpha_3\beta_4$ nicotinic receptor antagonist, wherein said first $\alpha_3\beta_4$ nicotinic receptor antagonist is 18-methoxycoronaridine or a pharmaceutically acceptable salt or solvate thereof and said second $\alpha_3\beta_4$ nicotinic receptor antagonist is bupropion or a pharmaceutically acceptable salt or solvate thereof.

30. A composition according to claim 29, wherein said first $\alpha_3\beta_4$ nicotinic receptor antagonist and said second $\alpha_3\beta_4$ nicotinic receptor antagonist are present in a weight ratio of from about 10:1 to about 1:10.

31. A composition according to claim 29, wherein said first $\alpha_3\beta_4$ nicotinic receptor antagonist and said second $\alpha_3\beta_4$ nicotinic receptor antagonist are present in a weight ratio of from about 5:1 to about 1:5.

32. A composition according to claim 29, wherein said composition is in the form of a tablet, capsule, granular dispersible powder, suspension, syrup, or elixir.

33. A composition according to claim 29, wherein said composition is in the form of a tablet or capsule and wherein said composition further comprises an inert diluent, a granulating agent, a disintegrating agent, a lubricating agent, or combinations thereof.

34. A method for treating nicotine addiction in a patient, said method comprising: administering to the patient a composition according to claim 29.

35. A method according to claim 34, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

36. A method according to claim 34, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

37. A method for treating amphetamine addiction in a patient, said method comprising: administering to the patient a composition according to claim 29.

38. A method according to claim 37, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

39. A method according to claim 37, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

40. A method for treating opioid addiction in a patient, said method comprising: administering to the patient a composition according to claim 29.

41. A method according to claim 40, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patients body weight per day.

42. A method according to claim 40, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

43. A composition comprising a first $\alpha_3\beta_4$ nicotinic receptor antagonist and a second $\alpha_3\beta_4$ nicotinic receptor antagonist, wherein said first $\alpha_3\beta_4$ nicotinic receptor antagonist is mecamylamine or a pharmaceutically acceptable salt or solvate thereof and said second $\alpha_3\beta_4$ nicotinic receptor antagonist is dextromethorphan or a pharmaceutically acceptable salt or solvate thereof.

44. A composition according to claim 43, wherein said first $\alpha_3\beta_4$ nicotinic receptor antagonist and said second $\alpha_3\beta_4$ nicotinic receptor antagonist are present in a weight ratio of from about 10:1 to about 1:10.

45. A composition according to claim 43, wherein said first $\alpha_3\beta_4$ nicotinic receptor antagonist and said second $\alpha_3\beta_4$ nicotinic receptor antagonist are present in a weight ratio of from about 5:1 to about 1:5.

46. A composition according to claim 43, wherein said composition is in the form of a tablet, capsule, granular dispersible powder, suspension, syrup, or elixir.

47. A composition according to claim 43, wherein said composition is in the form of a tablet or capsule and wherein said composition further comprises an inert diluent, a granulating agent, a disintegrating agent, a lubricating agent, or combinations thereof.

48. A method for treating nicotine addiction in a patient, said method comprising: administering to the patient a composition according to claim 43.

49. A method according to claim 48, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

50. A method according to claim 48, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

51. A method for treating amphetamine addiction in a patient, said method comprising: administering to the patient a composition according to claim 43.

52. A method according to claim 51, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

53. A method according to claim 51, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

54. A method for treating opioid addiction in a patient, said method comprising: administering to the patient a composition according to claim 43.

55. A method according to claim 54, wherein the first $\alpha_3\beta_4$ nicotinic receptor antagonist is administered in an amount of from about 0.01 to about 10 mg/kg of the patient's body weight per day and wherein the second $\alpha_3\beta_4$ nicotinic receptor antagonist is administered in an amount of from about 0.01 to about 10 mg/kg of the patient's body weight per day.

56. A method according to claim 54, wherein the first $\alpha_3\beta_4$ nicotinic receptor antagonist is administered in an amount of from about 0.1 to about 5 mg/kg of the patient's body weight per day and wherein the second $\alpha_3\beta_4$ nicotinic receptor antagonist is administered in an amount of from about 0.1 to about 5 mg/kg of the patient's body weight per day.

* * * * *